US011413024B2

(12) United States Patent
Dewey

(10) Patent No.: US 11,413,024 B2
(45) Date of Patent: Aug. 16, 2022

(54) SURGICAL RETRACTOR AND METHOD

(71) Applicant: Warsaw Orthopedic, Inc., Warsaw, IN (US)

(72) Inventor: Jonathan Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/986,443

(22) Filed: Aug. 6, 2020

(65) Prior Publication Data
US 2022/0039786 A1    Feb. 10, 2022

(51) Int. Cl.
*A61B 17/02* (2006.01)

(52) U.S. Cl.
CPC ........ *A61B 17/0206* (2013.01); *A61B 17/025* (2013.01); *A61B 17/0218* (2013.01); *A61B 2017/0256* (2013.01)

(58) Field of Classification Search
CPC ............ A61B 17/0206; A61B 17/0218; A61B 17/025
USPC .......... 606/90; 600/210, 214, 215, 216, 219, 600/222, 225
See application file for complete search history.

(56) References Cited

U.S. PATENT DOCUMENTS

| | | | |
|---|---|---|---|
| 2,450,194 A * | 9/1948 | Glaser | A61B 17/0206 600/232 |
| 4,239,036 A * | 12/1980 | Krieger | A61B 17/02 600/206 |
| 4,881,525 A | 11/1989 | Williams | |
| 5,908,382 A * | 6/1999 | Koros | A61B 17/0206 600/232 |
| 6,074,343 A * | 6/2000 | Nathanson | A61B 17/0206 600/214 |
| 6,527,710 B1 * | 3/2003 | Davidson | A61B 1/32 600/219 |
| 7,220,228 B2 | 5/2007 | Hu et al. | |
| 7,481,766 B2 | 1/2009 | Lee et al. | |
| 7,654,954 B1 * | 2/2010 | Phillips | A61B 17/0206 600/228 |
| 7,753,844 B2 | 7/2010 | Sharratt et al. | |
| 7,909,846 B1 * | 3/2011 | Taylor | A61B 17/0206 606/198 |
| 7,946,982 B2 | 5/2011 | Hamada | |
| 8,852,090 B2 * | 10/2014 | Friedrich | A61B 17/0293 600/228 |
| 9,113,853 B1 | 8/2015 | Casey et al. | |
| 9,220,507 B1 | 12/2015 | Patel et al. | |
| 9,271,712 B2 | 3/2016 | Kim | |
| 9,492,065 B2 | 11/2016 | Tesar et al. | |
| 2005/0113645 A1 * | 5/2005 | Sharratt | A61B 17/0206 600/227 |
| 2006/0089537 A1 * | 4/2006 | Schoellhorn | A61B 17/0206 600/217 |

(Continued)

FOREIGN PATENT DOCUMENTS

CN    101912282 A    1/2012

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A surgical instrument includes at least one blade defining a longitudinal axis and includes a distal member. An actuator is engageable with the member to rotate the member relative to the longitudinal axis to space tissue adjacent a surgical site. Surgical systems, constructs, implants, and methods are disclosed.

19 Claims, 12 Drawing Sheets

(56) References Cited

U.S. PATENT DOCUMENTS

2010/0256454 A1* 10/2010 Farley .................... A61B 17/02
                                                        600/210
2017/0172556 A1*  6/2017 Bass .................. A61B 17/0206
2019/0015089 A1*  1/2019 Rosenbaum ....... A61B 17/0206
2019/0231334 A1   8/2019 Serokosz et al.

* cited by examiner

SURGICAL RETRACTOR AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Surgical retractors may be employed during a surgical treatment to provide access and visualization of a surgical site. Such retractors space apart and support tissue and/or other anatomical structures to expose anatomical structures adjacent the surgical site and/ or provide a surgical pathway to the surgical site. This disclosure describes an improvement over these prior technologies.

SUMMARY

In one embodiment, a surgical instrument is provided. The surgical instrument includes at least one blade defining a longitudinal axis and including a distal member. An actuator is engageable with the member to rotate the member relative to the longitudinal axis to space tissue adjacent a surgical site. In some embodiments, surgical systems, constructs, implants, and methods are disclosed.

In one embodiment, the surgical instrument includes at least one blade defining a longitudinal axis and including a distal member. An actuator includes a linkage and is engageable with the member to rotate the member relative to the longitudinal axis between a first orientation and a second orientation to space tissue adjacent a surgical site.

In one embodiment, the surgical instrument includes at least one blade defining a longitudinal axis and including a distal member. An actuator includes a threaded shaft and is engageable with the member to fix the member in a selected orientation relative to the longitudinal axis to space tissue adjacent a surgical site.

BRIEF DESCRIPTION OF THE DRAWINGS

The present disclosure will become more readily apparent from the specific description accompanied by the following drawings, in which.

DETAILED DESCRIPTION

Figure 1:
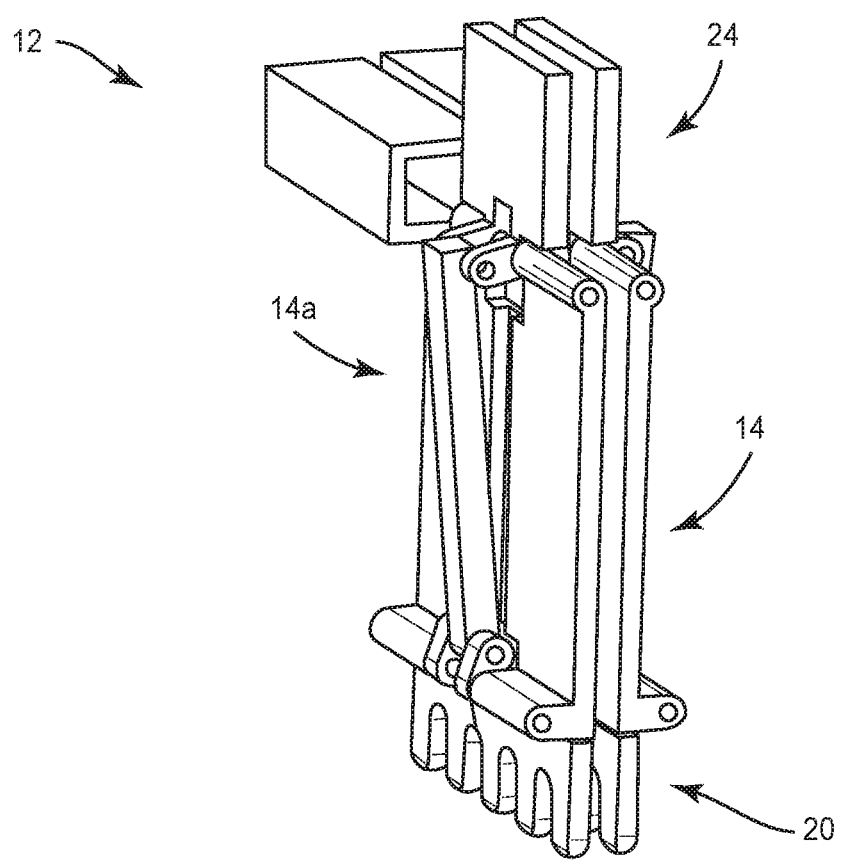
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine. In some embodiments, the systems and methods of the present disclosure comprise a surgical instrument, for example, one or more retractor blades configured to provide access and visualization of a surgical site, selective orientation, and positioning of surgical instrumentation and/or support of patient anatomy. In some embodiments, the present surgical system includes a surgical instrument, for example, a retractor including retractor blades having relatively movable tips. In some embodiments, the tips are configured to secure the blades with a surgical site. In some embodiments, the tips are configured to resist and/or prevent blade displacement, blade deformation, back out or play due to tissue creep, deformation, and/or inadvertent engagement, which may require repositioning of the blade during a procedure.

In some embodiments, the present surgical system includes a surgical instrument, for example, a retractor including one or more retractor blades having a tip configured to engage patient anatomy, for example, surrounding tissue in a configuration to provide securement of the retractor blade within a surgical site. In some embodiments, the surgical instrument includes a retractor that expands a surgical space at a surgical site without requiring an entirety of the retractor blade to engage tissue. This configuration reduces pressure placed upon tissue to reduce necrosis of the tissue. In some embodiments, the retractor is configured to reduce blade back out frequency from an incision, surgical space, and/or surgical site. In some embodiments, the retractor reduces tissue creep and repositioning of the retractor during a surgical procedure.

In some embodiments, the present surgical system includes a surgical instrument, for example, an articulating retractor that is inserted into a surgical site and employed with a method for treating a spine. In some embodiments, the retractor includes two blades having deployable tips. In some embodiments, the method includes the step of distracting the retractor to retract tissue to create a channel to work through during a surgical procedure. In some embodiments, the retractor is distracted and the tip retracts the tissue incrementally relative to the blade. In some embodiments, each blade of the retractor includes a latch for locking the tip into a tissue capturing orientation. In some embodiments, the method includes the step of rotating the latch to pivot the tip into a selected orientation, for example, a tissue capturing orientation. In some embodiments, as the tip is rotated, tissue is raised and is retained by the tip. In some embodiments, the method includes the step of further rotating the latch to pivot the tip into an orientation. In some embodiments, the method includes the step of further rotating the latch to pivot the tip into an orientation, thereby translating the tip into a locked, tissue capturing orientation. In some embodiments, the retractor includes a plurality of latches. In some embodiments, the retractor includes two latches.

In some embodiments, the present surgical system includes a surgical instrument including a retractor having a blade and an over-center mechanism configured to dispose a tip of the blade in a tissue capturing orientation. In some embodiments, the over-center mechanism includes a latch and a driving linkage. In some embodiments, the retractor includes a first orientation, for example, a non-deployed orientation and a second orientation, for example, a fully deployed orientation. In some embodiments, in the non-deployed orientation, the linkage includes a pivot which is not positioned over-center or through a neutral plane disposed between a latch pivot and a blade tip pivot, and the tip of the blade is disposed in a non-locked orientation. In some embodiments, in the deployed orientation, the linkage pivot is over-center and disposed in a relative position and/or orientation past the neutral plane, and as pressure is applied to the tip, the tip of the blade is disposed in a locked orientation. In some embodiments, the over-center mechanism is movable in one motion for locking the tip of the blade. In some embodiments, as the retractor is moved during use or when a patient is moved, the retractor will remain in the incision and prevent tissue creep at the surgical site. In some embodiments, a low-profile blade is provided during retractor insertion to minimize incision size. In some embodiments, the surgical instrument includes a tip disposable at a selected angle relative to a blade. In some embodiments, the blade and the tip form a steep slope, for example, a steep angle of incidence with surrounding tissue to prevent tissue from moving into the surgical site.

In some embodiments, the present surgical system includes a retractor including at least one blade having a threaded shaft. In some embodiments, the threaded shaft is configured to engage a linkage, for example, a bracket, and a tip of the blade. In some embodiments, the threaded shaft is rotated to orient the tip in a deployed orientation to capture tissue. In some embodiments, the threaded shaft is rotated in a series of one-half rotations. In some embodiments, the threaded shaft incrementally rotates the tip to capture tissue. In some embodiments, when the tip is in the deployed orientation, the blade and/or the tip includes a greater or lower profile relative to the retractor. In some embodiments, a surgeon can adjust the tip during surgery via the threaded shaft. In some embodiments, the retractor includes a quick release mechanism. In some embodiments, the quick release mechanism is configured to allow the tip to change from a deployed orientation to a non-deployed orientation quickly relative to when the threaded shaft is rotated to change orientations. In some embodiments, the quick-release mechanism is actuated and the tip is positioned in a linear orientation/non-deployed orientation relative to the threaded shaft to remove the retractor, blade, and/or the tip from an incision easily and/or quickly.

In some embodiments, the present surgical system includes a retractor including at least one blade. In some embodiments, a section of a tip of the blade is configured to retain tissue and a section of the blade is configured for retention within the incision. In some embodiments, various portions of the blade can be articulated. In some embodiments, only a portion of the blade is articulated. In some embodiments, only the tip of the blade is articulated or a significant portion of the blade is articulated. In some embodiments, an articulated blade or an articulated tip facilitates visualization of the bottom of the blade during use. In some embodiments, articulating the tip reduces pressure caused by the blade when pressed against tissue. In some embodiments, the blade is articulated at a middle section of the blade. In some embodiments, approximately three quarters of the blade from the tip to a proximal end is articulated. In some embodiments, the blade includes multiple articulating joints configured for anchoring and visualization.

In some embodiments, the retractor blade can be rotated into one or more orientations. In some embodiments, the tip is deployed separate of a body of the blade. In some embodiments, the tip of the blade includes one or more teeth or hooks to engage surrounding tissue. In some embodiments, each of the teeth or hooks articulate. In some embodiments, one or more of the teeth or hooks articulate separately from each other. In some embodiments, the teeth or hooks articulate in multiple stages.

In some embodiments, the present surgical system includes a retractor including a locking pawl mechanism. In some embodiments, the locking pawl mechanism can include indicia, for example, audible and/or tactile indicia when the blade is disposed in a selected orientation, for example, a deployed orientation for capturing tissue. In some embodiments, the present surgical system includes a retractor including a blade having multiple tabs disposed along a length of the blade. In some embodiments, the tabs are configured to engage with multiple blade tips for fixation along the length of the blade.

In some embodiments, the present surgical system can be employed with a method for treating a spine including the step of connecting and/or slidably engaging one or more surgical retractor blades with a mating retraction rack. In some embodiments, the method includes the step of manipulating the retraction rack to laterally translate the blades. In some embodiments, the method includes the step of rotating articulating blade tips at an angle via an actuator, thereby retracting an incision in a working surgical field.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone, and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-14, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate such as hydroxyapatite (HA), corraline HA, biphasic calcium phosphate, tricalcium phosphate, or fluorapatite, tricalcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected, or include fastening elements and/or instruments, as described herein.

Surgical system 10 includes a surgical instrument, for example, a surgical retractor 12 having retractor blades, for example, a blade 14 and a blade 14a, similar to blade 14 described herein. Blade 14 is configured to provide selective orientation and positioning of a surgical instrument and/or support of patient anatomy, for example, for engagement and/or fixation with surrounding tissue. In some embodiments, retractor 12 expands a surgical space at a surgical site without requiring the entirety of each blade 14, 14a to engage tissue, thereby reducing pressure placed upon tissue to reduce necrosis of the tissue.

Figure 2:
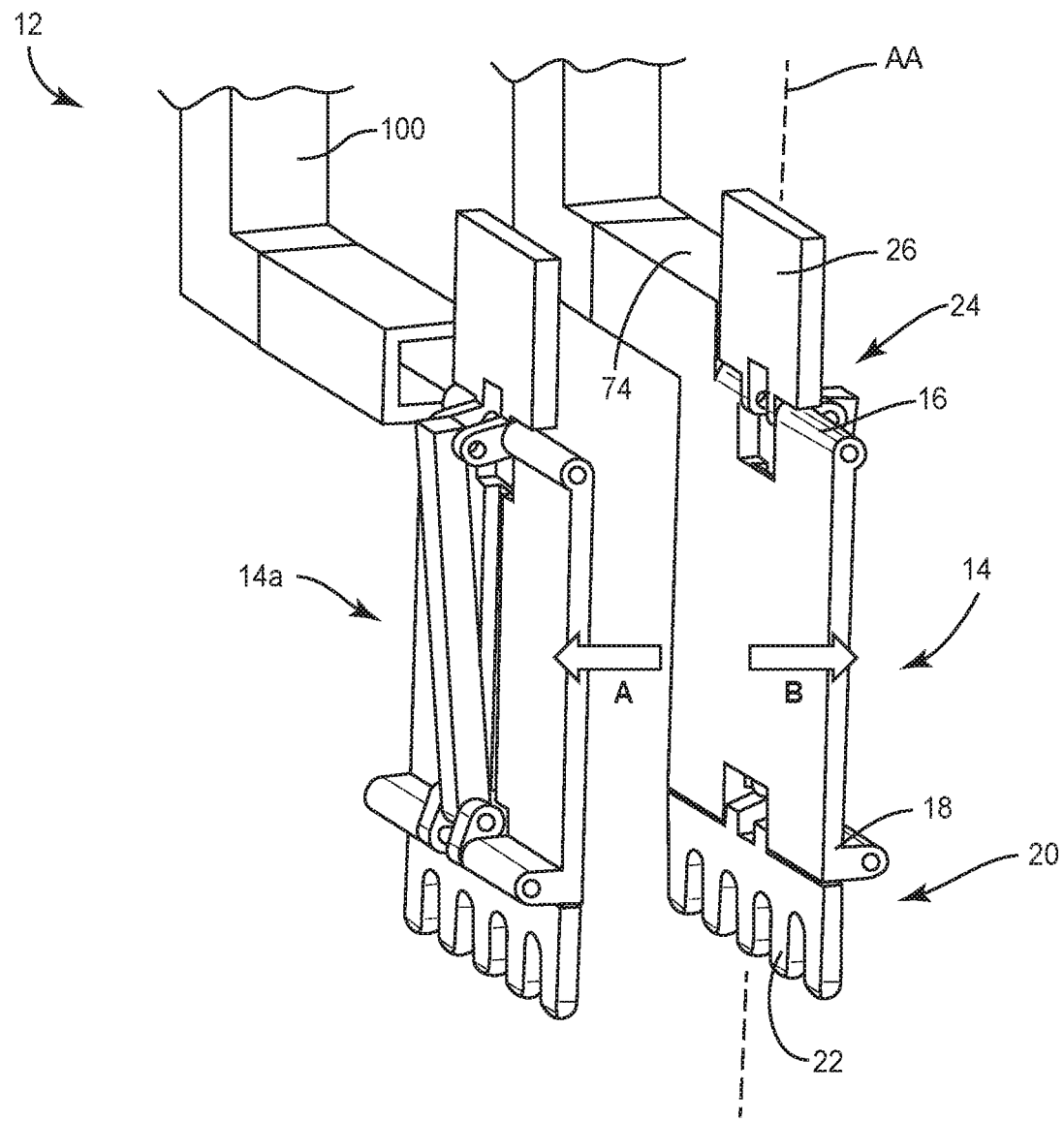
FIG. 2 is a perspective view of components of one embodiment of a surgical system in accordance with the principles of the present disclosure.

Blade 14 includes a proximal end 16 and a distal end 18, and defines a longitudinal axis AA, as shown in FIG. 2.

Blade 14 may have various cross-section configurations, for example, arcuate, cylindrical, oblong, rectangular, polygonal, undulating, irregular, uniform, non-uniform, consistent, variable, and/or U-shape. In some embodiments, blade 14 includes a cross-section configured to aid in visualization during x-ray and/or fluoroscopy. In some embodiments, blade 14 includes a minimum cross-section of material to reduce the footprint needed for insertion of blade 14 into an incision for spacing and retaining tissue. In some embodiments, blade 14 may have alternate surface configurations, for example, rough, undulating, corrugated, a series of peaks and valleys, porous, semi-porous, dimpled, polished and/or textured. In some embodiments, a surface configuration of blade 14 including corrugations and/or peaks-and-valleys, increases surface area contact of blade 14 with the tissue and spreads a retraction force over a large surface area of the tissue. In some embodiments, retractor 12 may include one or a plurality of blades 14.

Figure 11:
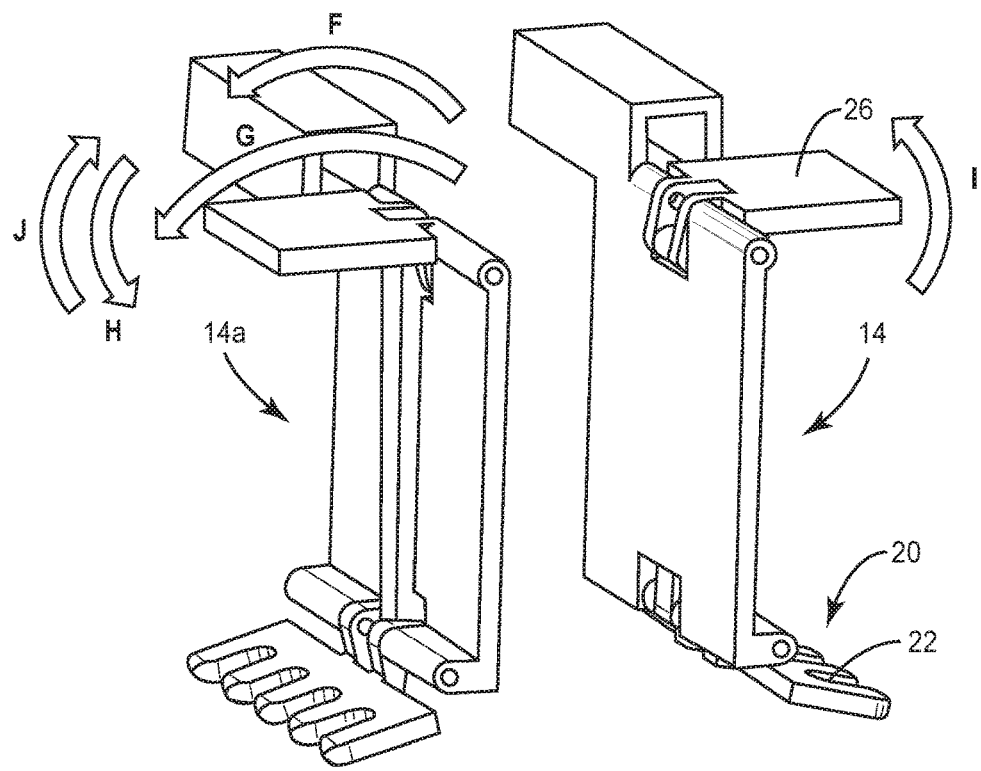
FIG. 11 is a perspective view of the components shown in FIG. 10.
Figure 14:
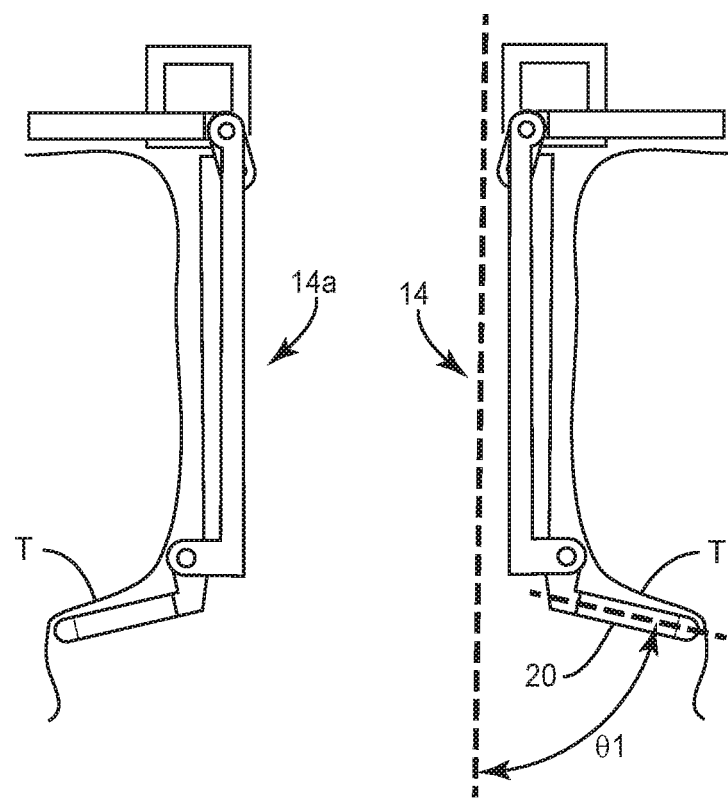
FIG. 14 is a side view of the components and tissue shown in FIG. 12.

End 18 includes a member, for example, a tip 20, as shown in FIG. 2. Tip 20 is configured to secure blade 14 with a surgical site and to engage patient anatomy, for example, for engagement and/or fixation with surrounding tissue. In some embodiments, tip 20 is the only portion of blade 14 that engages tissue. Tip 20 is rotatable relative to longitudinal axis AA between a non-deployed orientation and a fixed deployed orientation to dispose tip 20 in a tissue capturing orientation, as shown in FIGS. 2 and 11. In some embodiments, tip 20 is placed in the deployed orientation to capture and retain tissue, to reduce back out of blade 14 within the surgical site and/or to reduce tissue creep and/or repositioning of retractor 12 during a surgical procedure, as described herein. In the deployed orientation, tip 20 is selectively disposable at an angle, for example, an angle of incidence $\ominus 1$ in a range of 45 to 90 degrees relative to longitudinal axis AA to capture and retain tissue, as shown in FIG. 14 and described herein. Tip 20 may have various cross-section configurations, for example, arcuate, cylindrical, oblong, rectangular, polygonal, undulating, irregular, uniform, non-uniform, consistent, variable, and/or U-shape. In some embodiments, tip 20 may have alternate surface configurations, for example, rough, undulating, porous, semi-porous, dimpled, polished and/or textured.

Figure 10:
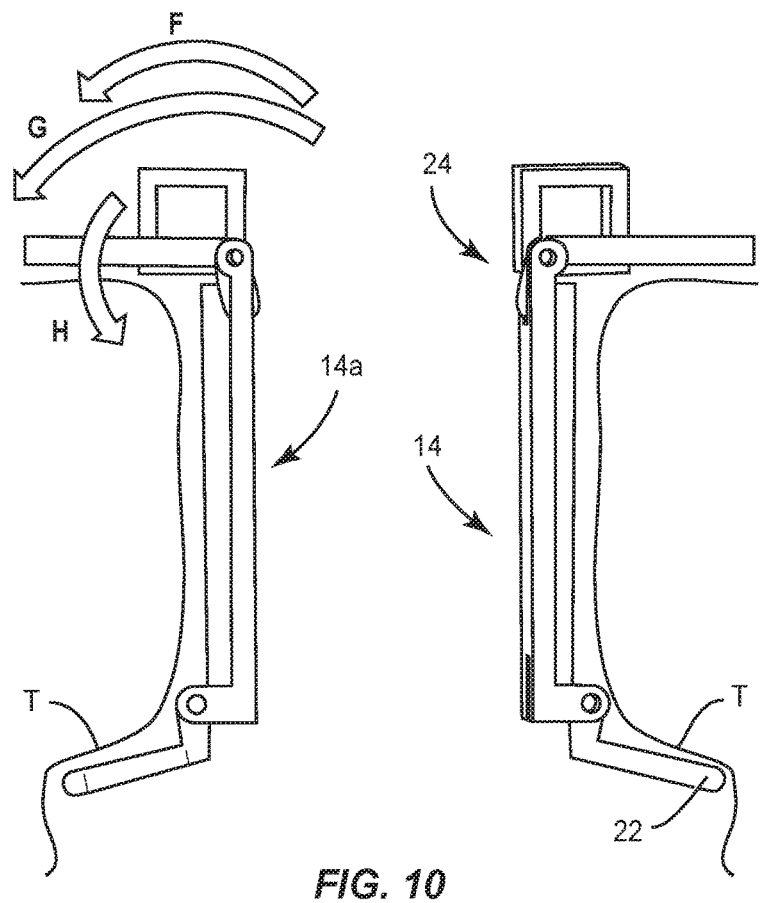
FIG. 10 is a side view of the components and tissue shown in FIG. 3.

Tip 20 includes teeth 22 configured to engage surrounding tissue, as shown in FIGS. 10 and 11, when tip 20 is in the deployed orientation. In some embodiments, tip 20 can include one tooth or a plurality of teeth 22. In some embodiments, teeth 22 includes hooks. In some embodiments, teeth 22 may have various cross-section configurations, for example, arcuate, cylindrical, oblong, rectangular, polygonal, undulating, irregular, uniform, non-uniform, consistent, variable, and/or U-shape. In some embodiments, teeth 22 may have alternate surface configurations, for example, rough, undulating, porous, semi-porous, dimpled, polished and/or textured. In some embodiments, tip 20 includes teeth 22 and static or stationary teeth disposed with end 18.

Figure 4:
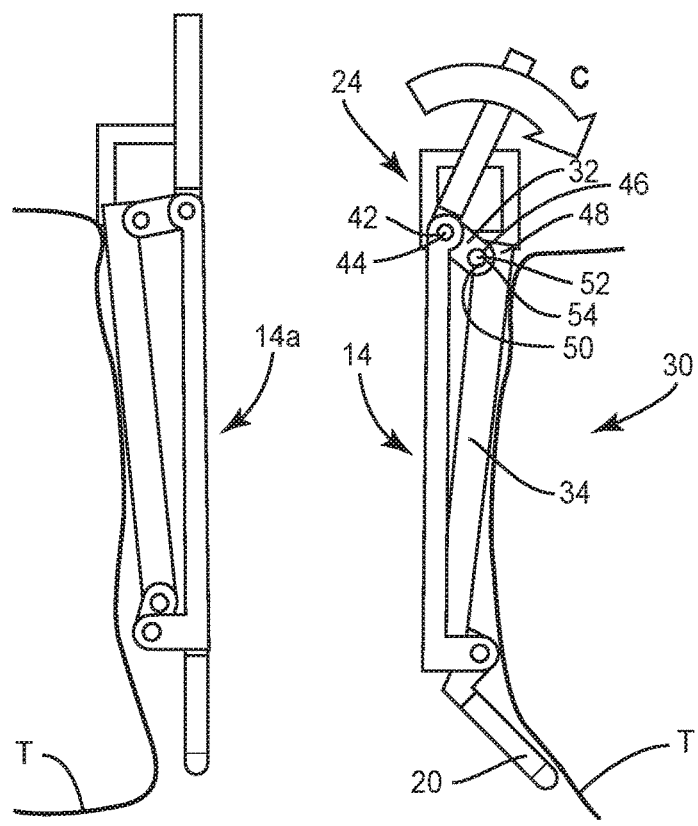
FIG. 4 is a side view of the components and tissue shown in FIG. 3.
Figure 5:
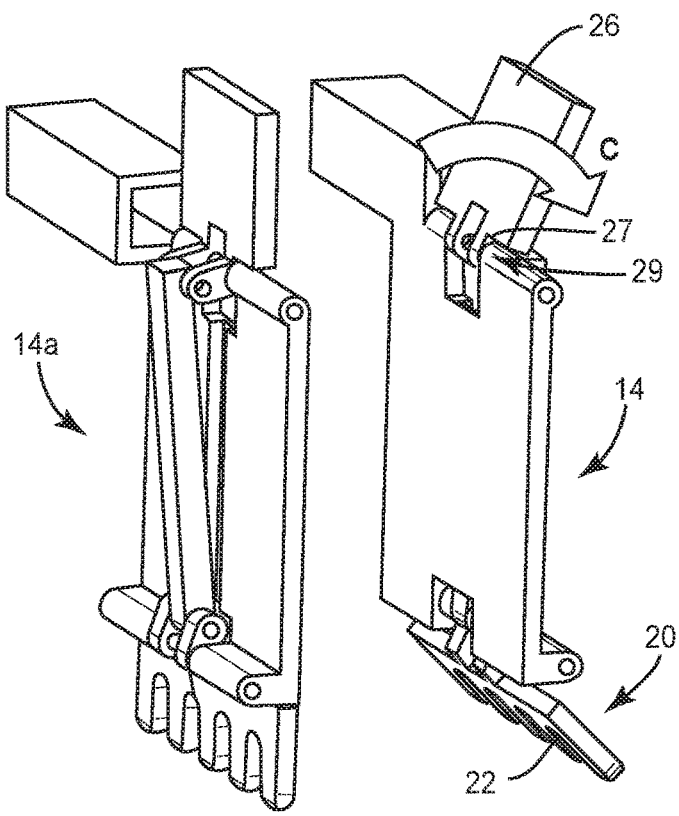
FIG. 5 is a perspective view of the components shown in FIG. 4.

Blade 14 includes an actuator 24 engageable with tip 20, as shown in FIG. 2. Actuator 24 is configured to rotate tip 20 between a non-deployed orientation, as shown in FIGS. 1 and 2, and a deployed orientation, as shown in FIGS. 10 and 11 relative to longitudinal axis AA to space tissue adjacent a surgical site. Actuator 24 includes an over-center latch 26 configured to lock tip 20 in the deployed orientation to capture tissue, as shown in FIGS. 10 and 11. Over-center latch 26 facilitates fixation of tip 20 in the deployed orientation while under tension. Over-center latch 26 includes an end 27 that includes a surface that defines an opening 29, as shown in FIG. 5. Opening 29 is configured for engagement with a pin 44, as shown in FIG. 4, to movably engage over-center latch 26 with end 16, as described herein. In some embodiments, over-center latch 26 is matingly engageable with a keeper to facilitate locking over-center latch 26.

Figure 3:
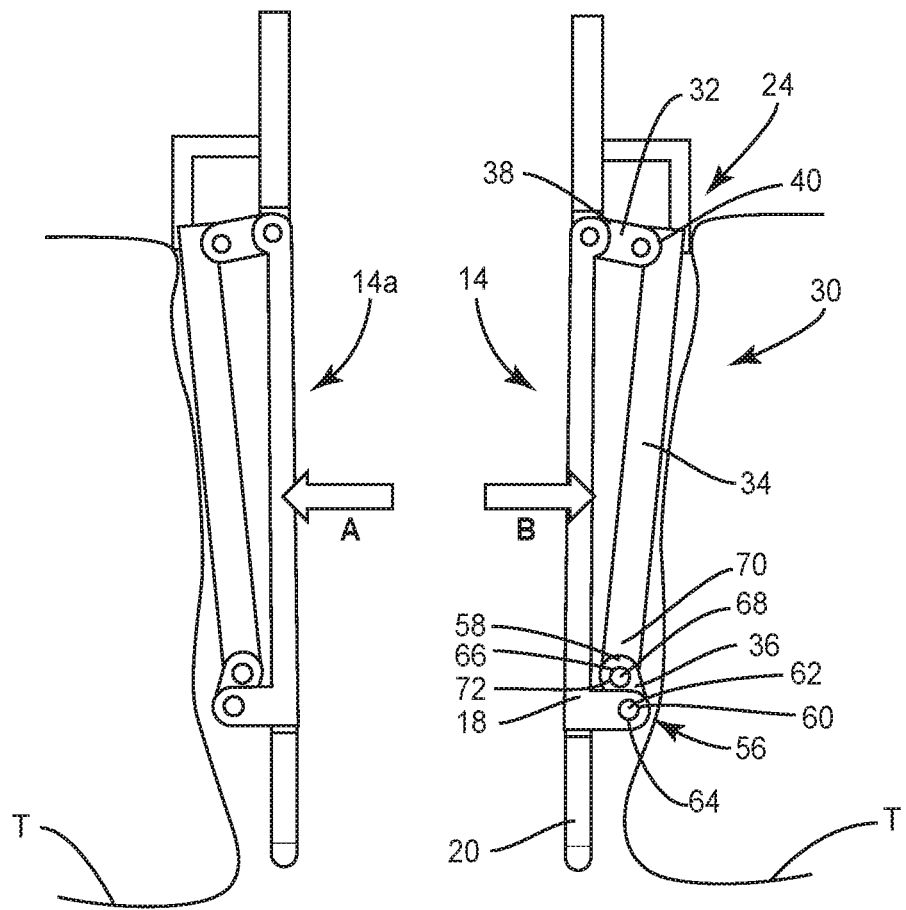
FIG. 3 is a side view of components of one embodiment of a surgical system in accordance with the principles of the present disclosure disposed with tissue.

Actuator 24 includes a linkage 30, as shown in FIGS. 3 and 4. Linkage 30 is engageable with over-center latch 26 and tip 20 to fix tip 20 in a selected orientation relative to longitudinal axis AA. Linkage 30 includes brackets 32, an intermediate bar 34 and brackets 36. In some embodiments, brackets 32, 36 have a yoke configuration. Brackets 32 each include an end 38 and an end 40, as shown in FIG. 3. End 38 includes a surface that defines an opening 42, as shown in FIG. 4. Opening 42 is configured for engagement with pin 44. A surface defines an opening 46 on end 16 of blade 14. Opening 46 is configured for engagement with pin 44 to engage blade 14 and over-center latch 26 with brackets 32.

Figure 12:
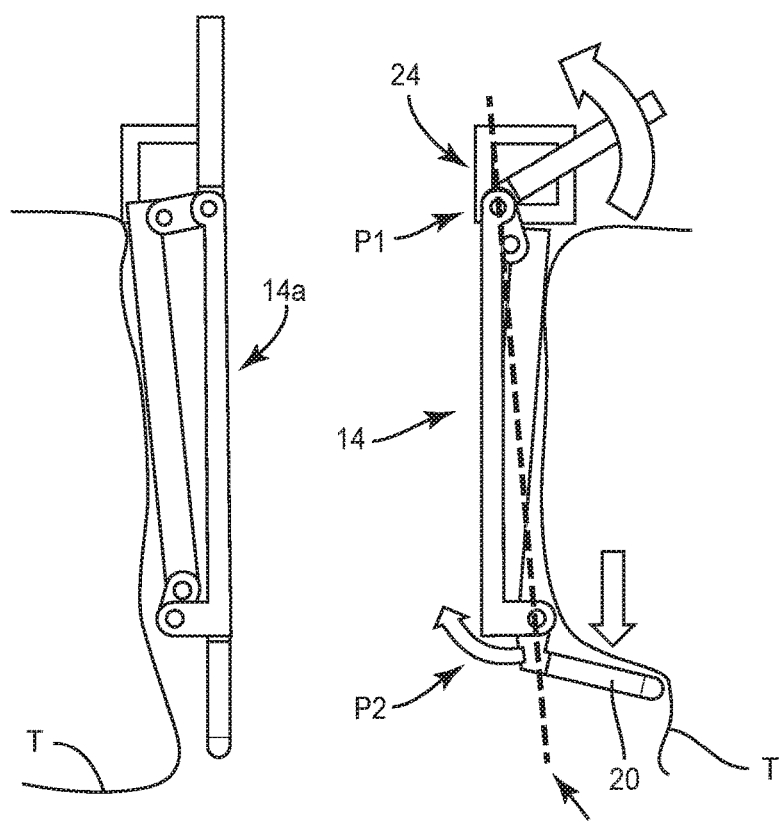
FIG. 12 is a side view of components of one embodiment of a surgical system in accordance with the principles of the present disclosure disposed with tissue.
Figure 13:
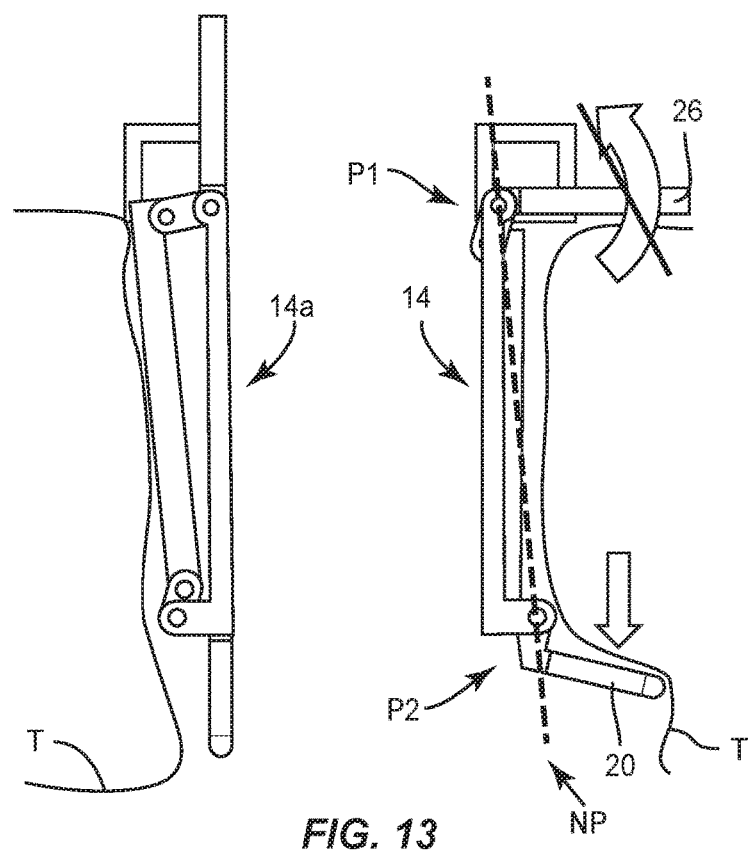
FIG. 13 is a side view of the components and tissue shown in FIG. 12.

End 40 of brackets 32 is configured for engagement with an end 48 of bar 34. End 40 includes a surface that defines an opening 50. Opening 50 is configured for engagement with a pin 52, as shown in FIG. 4. End 48 of bar 34 includes a surface that defines an opening 54. Opening 54 is configured for engagement with pin 52 to engage bar 34 with brackets 32. Engagement between brackets 32 and blade 14 with over-center latch 26 and engagement between brackets 32 and bar 34 creates a pivot point P1, as shown in FIGS. 12 and 13.

Brackets 36 each include an end 56 and an end 58, as shown in FIG. 3. End 56 includes a surface that defines an opening 60. Opening 60 is configured for engagement with a pin 62. A surface defines an opening 64 on end 18 of blade 14. Opening 64 is configured for engagement with pin 62 to engage blade 14 with brackets 36. End 58 includes a surface that defines an opening 66. Opening 66 is configured for engagement with a pin 68. An end 70 of bar 34 includes a surface that defines an opening 72. Opening 72 is configured for engagement with pin 68 to engage bar 34 with brackets 36. Engagement between brackets 36 with blade 14 and engagement between brackets 36 with bar 34 creates a pivot point P2, as shown in FIGS. 12 and 13. In some embodiments, blade 14, brackets 32, bar 34 and brackets 36 are a four-bar linkage or mechanism.

Figure 6:
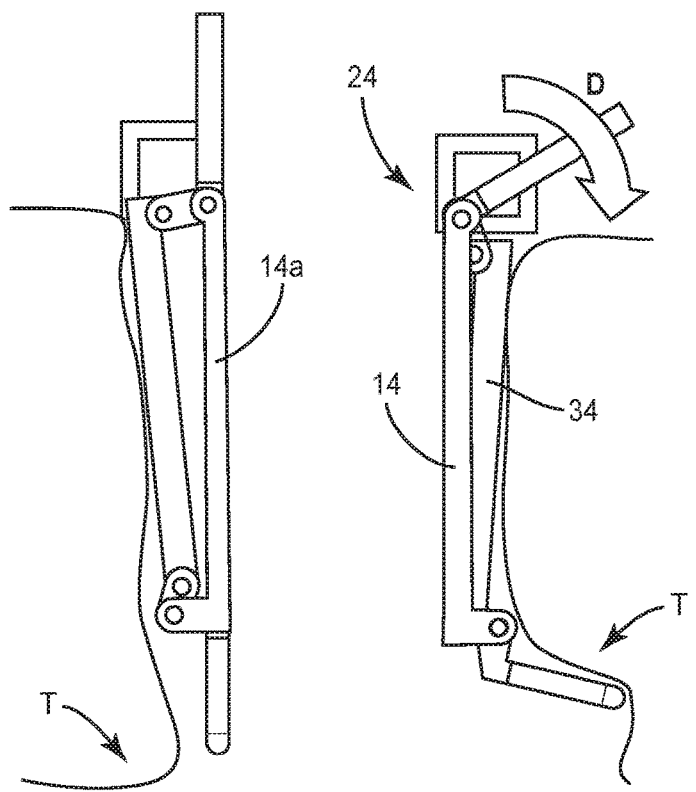
FIG. 6 is a side view of the components and tissue shown in FIG. 3.
Figure 7:
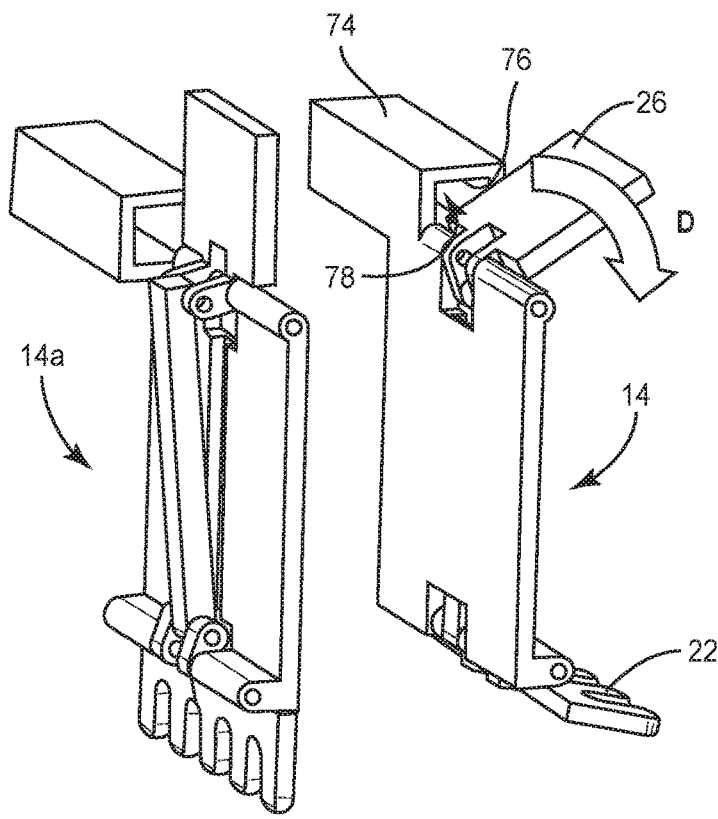
FIG. 7 is a perspective view of the components shown in FIG. 6.
Figure 8:
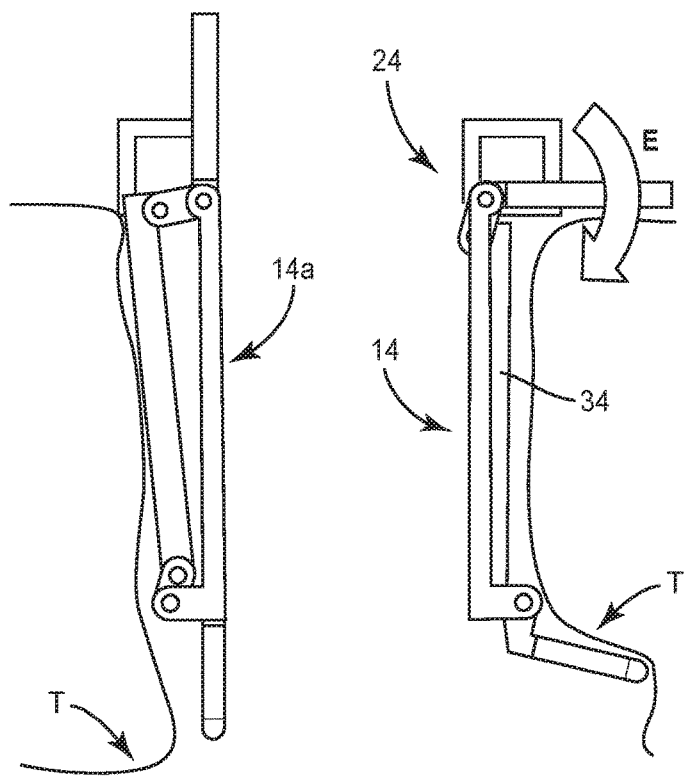
FIG. 8 is a side view of the components and tissue shown in FIG. 3.
Figure 9:
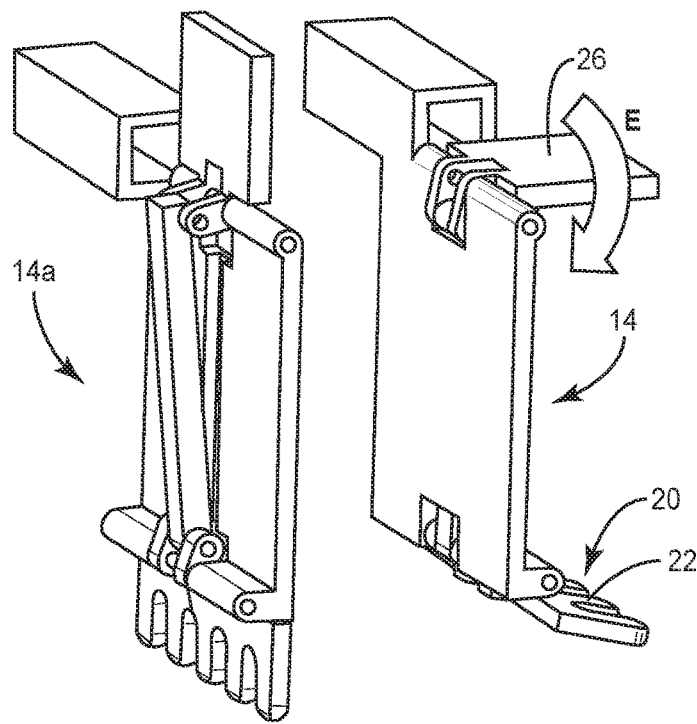
FIG. 9 is a perspective view of the components shown in FIG. 8.

Over-center latch 26 is rotated to incrementally rotate tip 20 relative to longitudinal axis AA between the non-deployed orientation and the deployed orientation. As shown in FIG. 1, tip 20 is in the non-deployed orientation. Over-center latch 26 is rotated and linkage 30 is translated such that tip 20 is rotated/pivoted into an orientation, as shown in FIGS. 4 and 5. Over-center latch 26 is rotated in the same direction and linkage 30 is translated such that tip 20 is rotated/pivoted into an orientation to engage tissue, as shown in FIGS. 6 and 7. Over-center latch 26 is rotated in the same direction and linkage 30 is translated such that tip 20 is rotated/pivoted into an orientation, for example, the tissue capturing orientation, as shown in FIGS. 8 and 9. In some embodiments, the tissue capturing orientation includes tip 20 being locked in a fully deployed orientation. In the fully deployed orientation, tissue is retained by tip 20 and tip 20 forms the angle of incidence $\ominus 1$ relative to longitudinal axis AA to prevent tissue from entering the surgical site, as shown in FIG. 14.

In some embodiments, the deployed orientation, the fully deployed orientation and/or the tissue capturing orientation includes pivot P1 of linkage 30 being disposed over-center and in a relative position and/or orientation past a neutral plane NP between pivot P1 and pivot P2, as shown in FIG.

13, such that when pressure is applied to tip 20, for example, via engagement with tissue, components of surgical system 10 and/or inadvertent contact, tip 20 remains in a relatively fixed and/or locked orientation. In some embodiments, the non-deployed orientation includes pivot P1 of linkage 30 being not disposed over-center and not disposed in a relative position and/or orientation past a neutral plane NP between pivot P1 and pivot P2, as shown in FIG. 12, such that when pressure is applied to tip 20, for example, via engagement with tissue, components of surgical system 10 and/or inadvertent contact, tip 20 is oriented in a non-locked orientation and tip 20 is movable relative to longitudinal axis AA. In some embodiments, over-center latch 26 and linkage 30 are movable in one motion for locking tip 20. In some embodiments, over-center latch 26 is unjointed, disconnected and/or pivoted from linkage 30 to facilitate folding, rotating and/or translating over-center latch 26 relative to linkage 30 without fixing tip 20 in a selected orientation, for example, the deployed orientation.

End 16 includes a mating portion 74, as shown in FIGS. 2 and 7. Portion 74 includes a surface 76 that defines an opening 78. Opening 78 is configured for disposal of a retraction rack 100. Blade 14 is attached with rack 100 for relative translation to space apart tissue. Blade 14 is attached with rack 100 such that blade 14 is movable in one or a plurality of degrees of freedom to one or a plurality of orientations relative to rack 100, stationary surgical equipment and/or a patient body in connection with a surgical procedure. In some embodiments, the degrees of movement in translation can include up, down, left, right, forward, and/or backward. In some embodiments, the degrees of movement in rotation can include tilting, swiveling, and/or pivoting in one or a plurality of directions. In some embodiments, blade 14 is independently and selectively movable relative to rack 100, stationary surgical equipment and/or the patient body. In some embodiments, one or a plurality of blades 14 may be attachable with rack 100.

In some embodiments, retractor 12 may be employed with various surgical instruments, for example, drivers, extenders, reducers, spreaders, distractors, clamps, forceps, elevators, and drills, which may be alternately sized and dimensioned, and arranged as a kit. In some embodiments, surgical system 10 may comprise the use of microsurgical and image guided technologies, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, surgical system 10, similar to the systems and methods described herein, is employed with a surgical procedure for treatment of a spinal disorder, such as those described herein, affecting a section of a spine of a patient. Surgical system 10 may also be employed with other surgical procedures. In some embodiments, surgical system 10 is employed to implant components, such as bone fasteners, rods, interbody devices, and plates, with a patient.

For example, with the body disposed in a selected orientation, for example, for a midline posterior TL surgical approach for a contra-lateral decompression and discectomy, a medical practitioner makes and/or creates an incision in tissue T, which includes soft tissue and/or muscle, to obtain access to a surgical site including affected vertebral levels of vertebrae. Tissue T is manipulated to space the tissue adjacent to the incision.

Surgical retractor 12, as described herein, is disposed within the incision for spacing and retaining tissue T. Blades 14, 14a, as described herein, are connected with rack 100, as shown in FIG. 2. Blades 14, 14a are relatively moveable and configured for insertion into tissue T. Blades 14, 14a are manipulated for movement by rack 100, relative to tissue T. Rack 100 is distracted to translate blades 14, 14a in opposing directions, as shown by arrows A and B in FIGS. 2 and 3, to expand and space the surgical site.

Over-center latch 26 is rotated manually by a user to incrementally rotate tip 20 relative to longitudinal axis AA between the non-deployed orientation and the deployed orientation, as described herein, to capture and retain tissue T. As shown in FIG. 1, tip 20 can be initially disposed in the non-deployed orientation. For example, to deploy tip 20 of blade 14, over-center latch 26 of blade 14 is initially rotated manually, in a direction shown by arrow C in FIGS. 4 and 5, and linkage 30 is translated such that tip 20 of blade 14 rotates/pivots from the non-deployed orientation. As shown in FIGS. 6 and 7, over-center latch 26 of blade 14 is further rotated, in a direction shown by arrow D, such that linkage 30 of blade 14 further rotates tip 20 of blade 14 to manipulate tissue T for spacing and retaining tissue T. Over-center latch 26 of blade 14 is further rotated, in a direction shown by arrow E in FIGS. 8 and 9, such that linkage 30 of blade 14 rotates tip 20 of blade 14 into an orientation, for example, a tissue capturing orientation and/or a fully deployed and locked orientation, as described herein, at a selected angle for spacing and retaining tissue T in connection with maintaining the surgical working channel and/or surgical pathway. In the tissue capturing orientation, tip 20 is in the deployed orientation and teeth 22 assist in retaining the tissue T.

Similar to blade 14, tip 20 of blade 14a is initially disposed in the non-deployed orientation, as shown in FIG. 1, and over-center latch 26 of blade 14a is rotated manually, in a direction shown by arrow F in FIGS. 10 and 11, such that linkage 30 of blade 14a translates to rotate and deploy tip 20 of blade 14a from the non-deployed orientation. As shown in FIGS. 10 and 11, over-center latch 26 of blade 14a is further rotated, in a direction shown by arrow G, such that linkage 30 of blade 14a further rotates tip 20 of blade 14a to manipulate tissue T for spacing and retaining tissue T. Over-center latch 26 of blade 14a is further rotated, in a direction shown by arrow H in FIGS. 10 and 11, such that linkage 30 further rotates tip 20 into an orientation, for example, a tissue capturing orientation and/or a fully deployed and locked orientation, as described herein, at a selected angle for spacing and retaining tissue T in connection with maintaining the surgical working channel and/or surgical pathway.

In some embodiments, pilot holes or the like are made in vertebrae adjacent the intervertebral space for receiving bone fasteners and/or attaching spinal constructs, which may include rods and plates. An inserter is attached with the implants and/or spinal constructs for delivery adjacent to a surgical site for implantation adjacent one or more vertebra and/or intervertebral spaces of the vertebral levels. In some embodiments, blades 14, 14a may include one or more guidance elements, for example, channels, groves, walls, and/or barriers that facilitate guidance of bone fasteners, spinal constructs and/or surgical instruments, for example, drivers, interbody inserters, disc preparation instruments, retractors (e.g., nerve root retractors), extenders, reducers, spreaders, distractors, clamps, forceps, elevators, and drills into the surgical site.

Upon completion of a procedure, as described herein, the surgical instruments, assemblies, and non-implanted components of surgical system 10 are removed and the incision(s) are closed. For example, to remove retractor 12 from the incision and/or tissue T, over-center latches 26 of blades 14, 14*a* are rotated to rotate tips 20 relative to longitudinal axis AA between the deployed orientation and the non-deployed orientation. As shown in FIG. 11, over-center latch 26 of blade 14 is rotated, in a direction shown by arrow I, such that linkage 30 of blade 14 rotates tip 20 of blade 14 into the non-deployed orientation to disengage tip 20 and/or teeth 22 from tissue T. Over-center latch 26 of blade 14*a* is rotated, in a direction shown by arrow J, such that linkage 30 of blade 14*a* rotates tip 20 of blade 14*a* into the non-deployed orientation to disengage tip 20 and/or teeth 22 from tissue T. Blades 14, 14*a* are then removed from the incision.

One or more of the components of surgical system 10 can be made of radiolucent materials such as polymers. Radiopaque markers may be included for identification under x-ray, fluoroscopy, CT, or other imaging techniques. In some embodiments, the use of surgical navigation, micro-surgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

Figure 15:
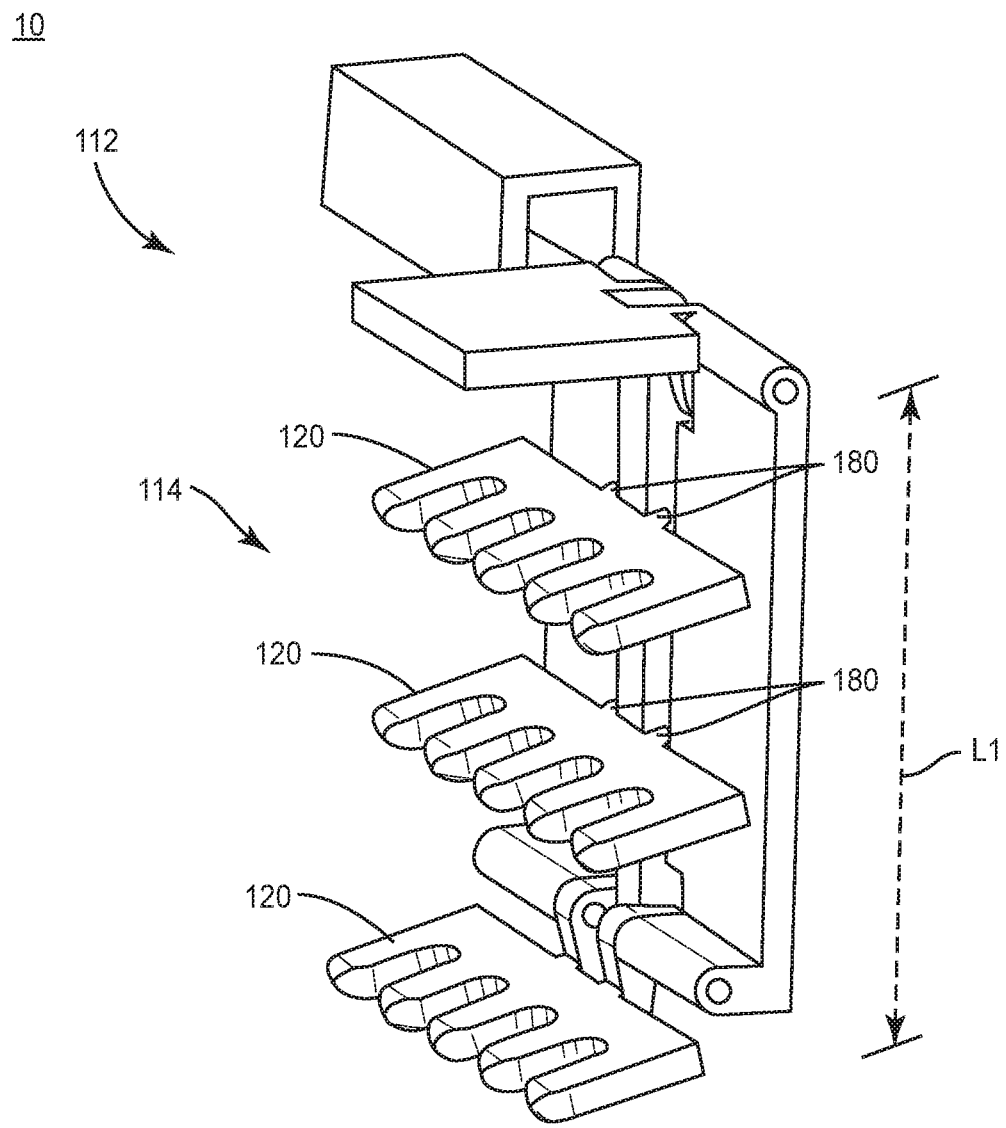
FIG. 15 is a perspective view of components of one embodiment of a surgical system in accordance with the principles of the present disclosure.

In one embodiment, as shown in FIG. 15, surgical system 10, similar to the systems and methods described herein, includes a retractor 112, similar to retractor 12 described herein. Retractor 112 includes a blade 114 that includes one or more tabs 180 disposed along a length L1 of blade 114. Tabs 180 are configured for engagement with blade tips 120 such that multiple tips 120 can be disposed along length L1 of blade 114 for capturing and retaining tissue. In some embodiments, retractor 112 includes one or a plurality of blades 114.

Figure 16:
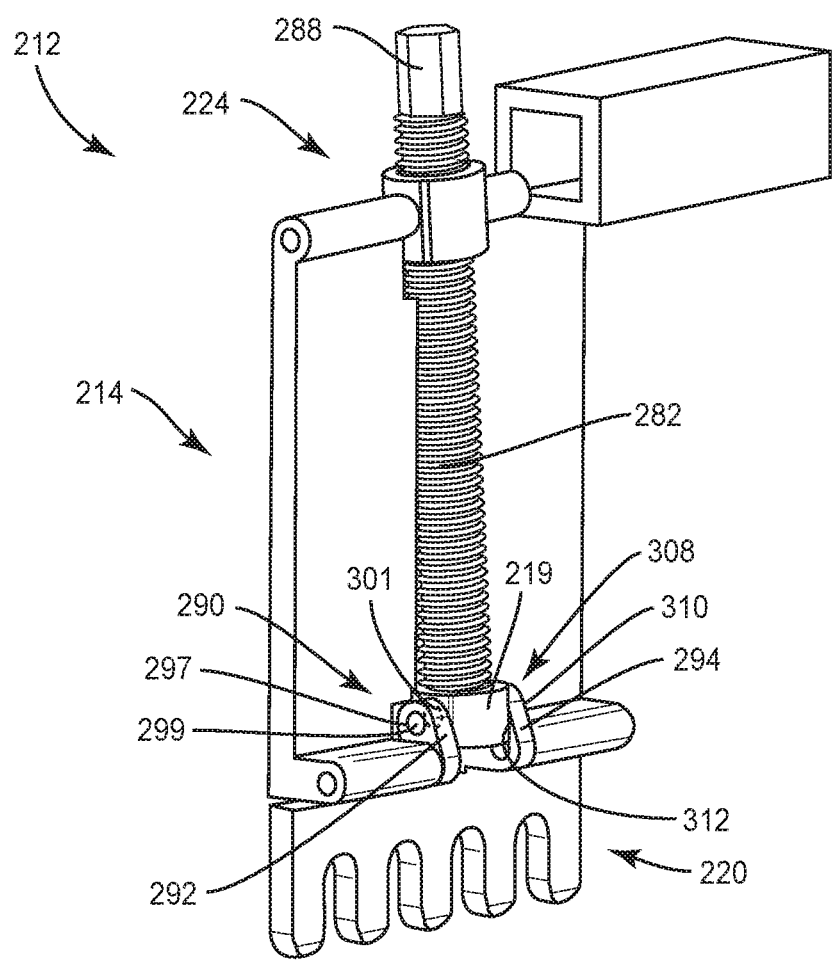
FIG. 16 is a perspective view of components of one embodiment of a surgical system in accordance with the principles of the present disclosure.
Figure 17:
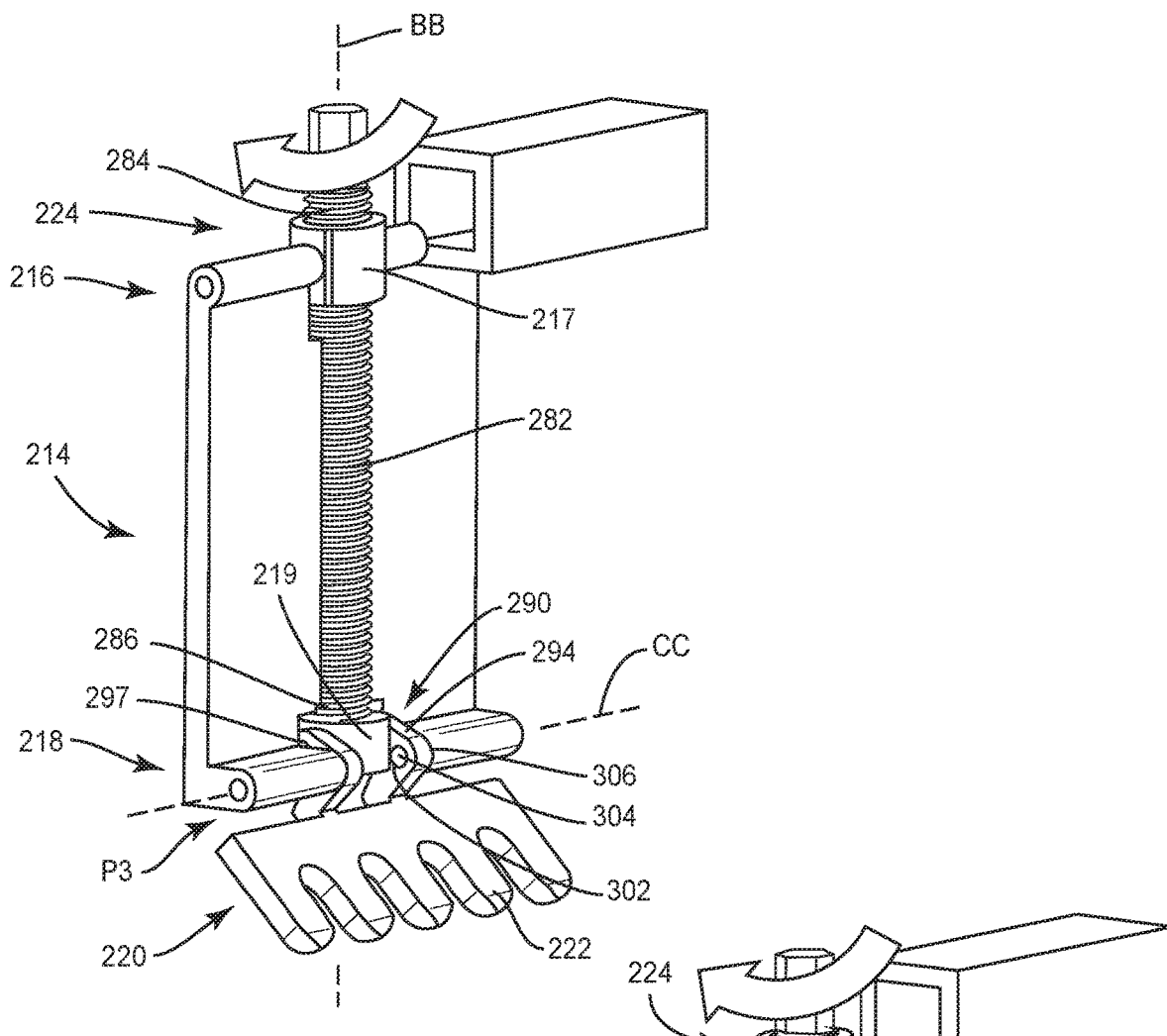
FIG. 17 is a perspective view of the components of FIG. 16.
Figure 18:
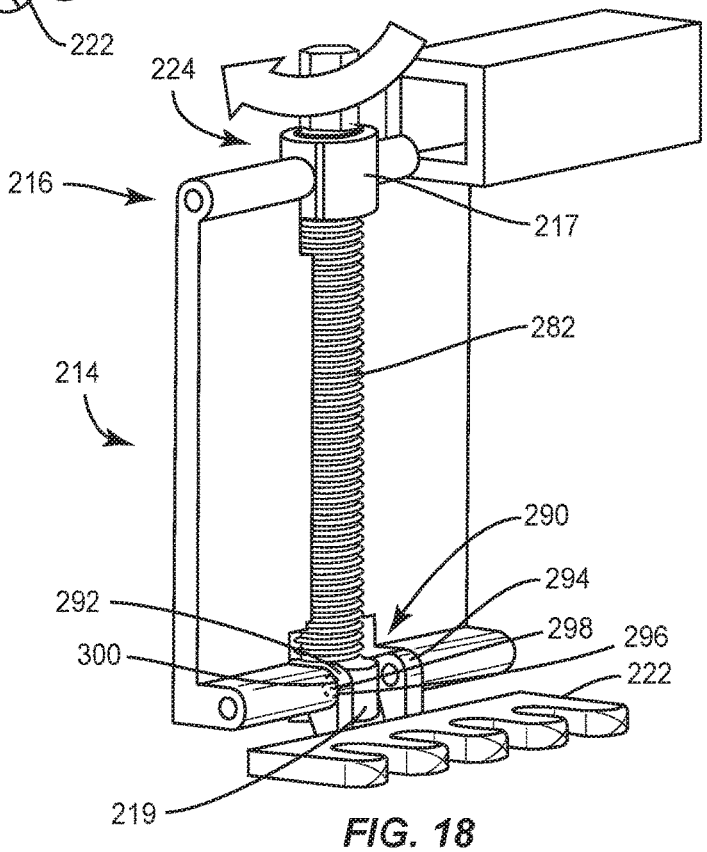
FIG. 18 is a perspective view of the components of FIG. 16.

In one embodiment, as shown in FIGS. 16-18, surgical system 10, similar to the systems and methods described herein, includes a retractor 212, similar to retractor 12 described herein, which includes a blade 214, as shown in FIG. 16. Blade 214, similar to blade 14 described above includes a proximal end 216 and a distal end 218 having a longitudinal axis BB disposed therebetween, as shown in FIG. 17. In some embodiments, retractor 212 may include one or a plurality of blades 214.

End 218 includes a member, for example, a tip 220, as shown in FIGS. 16-18, similar to tip 20 described herein. Tip 220 is rotatable relative to longitudinal axis BB between a non-deployed orientation and a fixed deployed orientation, to dispose tip 220 in a tissue capturing orientation, as shown in FIGS. 16 and 18. Tip 220 includes teeth 222 configured to engage surrounding tissue, as shown in FIG. 17. In some embodiments, tip 220 can include one tooth or a plurality of teeth 222. In some embodiments, teeth 222 includes hooks.

Blade 214 includes an actuator 224 engageable with tip 220 to fix tip 220 in a selected orientation, for example, between a non-deployed orientation and a deployed orientation, as described herein, relative to longitudinal axis BB to space tissue adjacent a surgical site. Actuator 224 includes a threaded shaft 282 engaged with end 216 via an internally threaded collar 217 and end 218 via a cup 219, as shown in FIG. 18. Rotation of shaft 282 translates/drives cup 219 to incrementally adjust tip 220 relative to longitudinal axis BB into a selected orientation, for example, a tissue capturing orientation.

Shaft 282 includes a proximal end 284 and a distal end 286, as shown in FIG. 17. End 284 includes a portion 288 configured for engagement and manipulation by a user to rotate shaft 282. Shaft 282 has a cylindrical cross-section configuration and includes an outer surface having an external thread form. In some embodiments, the thread form may include a single thread turn or a plurality of discrete threads. In some embodiments, all or only a portion of shaft 282 may have alternate cross-section configurations, for example, oval, oblong, triangular, square, polygonal, irregular, uniform, non-uniform, offset, staggered, undulating, arcuate, variable and/or tapered.

Actuator 224 includes a linkage 290 engageable with shaft 282 and tip 220. Linkage 290 includes an angled bracket 292 and an angled bracket 294 disposed parallel to bracket 292, as shown in FIG. 18. Brackets 292, 294 are fixed with tip 220 and configured for engagement with blade 214 along a transverse axis CC, as shown in FIG. 17. Bracket 292 includes a surface that defines an opening 296 configured for engagement with a pin 298 to engage bracket 292 with an opening 300 of end 218 of blade 214, as shown in FIG. 18. Bracket 292 includes a surface that defines an opening 297 configured for engagement with a pin 299 to engage bracket 292 and pin 299 with an opening 301 of cup 219, as shown in FIG. 16. Pin 299 is configured for engagement with shaft 282 through opening 301, as described herein.

Bracket 294 includes a surface that defines an opening 302 configured for engagement with a pin 304 to engage bracket 294 with an opening 306 of end 218 of blade 214, as shown in FIG. 17. Bracket 294 includes a surface that defines an opening 308 configured for engagement with a pin 310 to engage bracket 294 and pin 310 with an opening 312 of cup 219, as shown in FIG. 16. Pin 310 is configured for engagement with shaft 282 through opening 312, as described herein.

Fixation between brackets 292, 294 with tip 220 and engagement between brackets 292, 294 and pins 298, 304 with blade 214 creates a pivot point P3, as shown in FIG. 17. Brackets 292, 294 and pins 299, 310 are engageable with shaft 282 through openings 301, 312, in cup 219, as shown in FIGS. 17 and 18. Pins 299, 310 rotate relative to axis BB as shaft 282 is rotated, and rotation of shaft 282 incrementally rotates tip 220 about axis CC into a selected orientation, for example, a tissue capturing orientation. In some embodiments, openings 296, 297 are connected by an open slot. In some embodiments, bracket 292 includes a slot configured for disposal of pin 299 such that as shaft 282 drives cup 219, pin 299 translates along the slot to incrementally adjust tip 220. In some embodiments, openings 302, 308 are connected by an open slot. In some embodiments, bracket 294 includes a slot configured for disposal of pin 310 such that as shaft 282 drives cup 219, pin 310 translates along the slot to incrementally adjust tip 220.

In some embodiments, shaft 282 is rotated in a series of one-half rotations. In some embodiments, shaft 282 provides integral adjustments of tip 220 rotation relative to axis BB. In some embodiments, when tip 220 is in a fixed deployed orientation, retractor 212 and/or tip 220 includes a greater or lower profile relative to axis BB.

In some embodiments, actuator 224 includes a quick release mechanism configured to release tip 220 from the deployed orientation to the non-deployed orientation without rotation of shaft 282. In some embodiments, the quick-release mechanism is actuated and tip 220 is positioned in a linear orientation/non-deployed orientation relative to the shaft 282 to remove retractor 212 and/or tip 220 from an incision easily and quickly relative to standard retractor removal.

In some embodiments, actuator 24 and/or actuator 224 includes a ratchet having a locking pawl, a latch or a clutch. In some embodiments, the locking pawl is configured to engage with the ratchet and prevent the ratchet from reversing direction such that when tips 20, 120 and/or 220 is rotated relative to longitudinal axis AA and/or longitudinal axis BB and positioned in a deployed orientation, the locking pawl will lock, preventing tips 20, 120 and/or 220 from undesired movement. In some embodiments, the locking pawl prevents tips 20, 120 and/or 220 from being positioned in an orientation that is not fully over-center such that P1 is not disposed in a relative position and/or orientation past the neutral plane.

In some embodiments, tips 20, 120 and/or 220 are deployed separate of a body of blade 14, 114 and/or 214 for customization during usage. In some embodiments, tips 14, 114 and/or 214 include one or more articulating hooks or teeth 22, 222. In some embodiments, one or more hooks or teeth can articulate separately from each other. In some embodiments, the hooks or teeth can be articulated in multiple stages.

In some embodiments, blade 14, 114 and/or 214 includes a cross-section configured to aid in visualization during x-ray and/or fluoroscopy. In some embodiments, blade 14, 114 and/or 214 has a minimum cross-section to reduce obstruction of the surgical view. In some embodiments, the cross-section of blade 14, 114 and/or 214 minimizes radiographic blocking. In some embodiments, blades 14, 114 and/or 214 are radiolucent. In some embodiments, blade 14, 114 and/or 214 can be made from stainless steel and/or plastic. In some embodiments, all or a portion of blade 14, 114 and/or 214 is made from a mesh or perforated material such that one or more openings in the mesh and/or perforated material provide visualization of the surgical site and one or more solid portions of the mesh and/or the perforated material provide strength and/or rigidity to blade 14, 114 and/or 214.

In some embodiments, blade 14, 114 and/or 214 and/or tip 20 and/or 120 include one or more openings configured for disposal of a stabilization pin engaging with vertebral tissue to fix and/or stabilize one or more components of surgical system 10, for example, blade 14, 114 and/or 214 and/or tip 20 and/or 120 with such vertebral tissue.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    at least one blade defining a longitudinal axis and including a distal member including a tip; and
    an actuator engageable with the member to rotate the tip relative to the longitudinal axis to space tissue adjacent a surgical site, the actuator including a latch connected to a proximal end of the at least one blade along a transverse axis, the latch being rotatable about the transverse axis to rotate the tip relative to the at least one blade, and the actuator including a ratchet having a locking pawl, the pawl configured to lock when the tip is rotated relative to the longitudinal axis and positioned in a deployed orientation.

2. A surgical instrument as recited in claim 1, wherein the latch includes an over-center latch configured to fix the tip in a selected orientation relative to the longitudinal axis.

3. A surgical instrument as recited in claim 1, wherein the tip is rotatable relative to the longitudinal axis between a first orientation and a second orientation such that the latch locks the tip in a tissue capturing orientation.

4. A surgical instrument as recited in claim 1, wherein the tip is rotatable relative to the longitudinal axis between a non-deployed orientation and the deployed orientation such that the tip is disposed in a tissue capturing orientation.

5. A surgical instrument as recited in claim 1, wherein the tip is selectively disposable at an angle in a range of 45 to 90 degrees relative to the longitudinal axis.

6. A surgical instrument as recited in claim 1, wherein the actuator includes a linkage having at least one bracket and an intermediate bar.

7. A surgical instrument as recited in claim 6, wherein the latch includes an over-center latch, the latch configured to dispose the tip in a tissue capturing orientation.

8. A surgical instrument as recited in claim 6, wherein the latch is engageable with the linkage and configured to fix the tip in a selected orientation relative to the longitudinal axis.

9. A surgical instrument as recited in claim 1, wherein the tip has at least one tooth.

10. A surgical instrument of claim 1, wherein the transverse axis is disposed perpendicular relative to the longitudinal axis.

11. A surgical instrument of claim 1, wherein the at least one blade includes one or more tabs disposed along a length of the at least one blade configured for engagement with one or more tips.

12. A surgical instrument comprising:
    at least one blade defining a longitudinal axis and including a distal member including a tip; and
    an actuator including a linkage and being engageable with the tip to rotate the tip relative to the longitudinal axis between a first orientation and a second orientation to space tissue adjacent a surgical site, the actuator including a latch connected to a proximal end of the at least one blade along a transverse axis, the latch being rotatable about the transverse axis to rotate the tip relative to the at least one blade, and the actuator including a ratchet having a locking pawl, the pawl configured to lock when the tip is rotated relative to the longitudinal axis and positioned in a deployed orientation.

13. A surgical instrument as recited in claim 12, wherein the latch includes an over-center latch configured to fix the tip in a selected orientation relative to the longitudinal axis.

14. A surgical instrument of claim 12, wherein the tip is rotatable relative to the longitudinal axis between the first orientation and the second orientation such that the latch locks the tip in a tissue capturing orientation.

15. A surgical instrument of claim 12, wherein the linkage includes at least one bracket and an intermediate bar.

16. A surgical instrument comprising:
    at least one blade defining a longitudinal axis and including a distal member including a tip; and
    an actuator including a threaded shaft and being threadingly engageable with a proximal end of the member and directly connected with the tip to rotate the tip to space tissue adjacent a surgical site, and the actuator including a ratchet having a locking pawl, the pawl configured to lock when the tip is rotated relative to the longitudinal axis and positioned in a deployed orientation.

17. A surgical instrument of claim 16, wherein a linkage having at least one bracket is engageable with the threaded shaft and the member, and rotation of the threaded shaft incrementally adjusts the tip in a selected tissue capturing orientation.

18. A surgical instrument of claim 16, wherein the threaded shaft is fully threaded.

19. A surgical instrument of claim 16, wherein the threaded shaft engages with an internally threaded collar of a proximal end of the at least one blade, and the threaded shaft engages with a cup of a distal end of the at least one blade.

\* \* \* \* \*